United States Patent
Anderson et al.

(10) Patent No.: US 7,904,146 B2
(45) Date of Patent: Mar. 8, 2011

(54) TRANSDERMAL SYSTEMS FOR THE DELIVERY OF IONIC AGENTS DIRECTLY TO OPEN WOUNDS AND SURGICALLY REPAIRED INCISIONS

(75) Inventors: Carter R. Anderson, Inver Grove Heights, MN (US); Russell L. Morris, Lindstrom, MN (US); Robert Cohen, Eden Prairie, MN (US)

(73) Assignee: Travanti Pharma Inc., Mendota Heights, MN (US)

( * ) Notice: Subject to any disclaimer, the term of this patent is extended or adjusted under 35 U.S.C. 154(b) by 39 days.

(21) Appl. No.: 11/937,769

(22) Filed: Nov. 9, 2007

(65) Prior Publication Data
US 2008/0114284 A1    May 15, 2008

Related U.S. Application Data

(60) Provisional application No. 60/865,471, filed on Nov. 13, 2006.

(51) Int. Cl.
*A61N 1/30* (2006.01)
*A61M 31/00* (2006.01)
*A61F 13/00* (2006.01)

(52) U.S. Cl. ............................. 604/20; 604/501; 424/449

(58) Field of Classification Search ..................... 604/20, 604/131, 890.1, 501; 424/449
See application file for complete search history.

(56) References Cited

U.S. PATENT DOCUMENTS

| | | | |
|---|---|---|---|
| 4,927,408 A | 5/1990 | Haak et al. | |
| 5,358,483 A | 10/1994 | Sibalis | |
| 5,458,569 A | 10/1995 | Kirk, III et al. | |
| 5,466,217 A | 11/1995 | Myers et al. | |
| 5,533,971 A | 7/1996 | Phipps | |
| 5,547,681 A * | 8/1996 | Clark et al. | 424/449 |
| 5,605,536 A | 2/1997 | Sibalis | |
| 5,651,768 A | 7/1997 | Sibalis | |
| 5,685,837 A | 11/1997 | Horstmann | |
| 6,383,511 B1 | 5/2002 | Cassel | |
| 6,421,561 B1 | 7/2002 | Morris | |
| 6,560,483 B1 | 5/2003 | Kumar et al. | |
| 6,645,521 B2 | 11/2003 | Cassel | |
| 6,653,014 B2 | 11/2003 | Anderson et al. | |
| 6,745,071 B1 | 6/2004 | Anderson et al. | |

(Continued)

OTHER PUBLICATIONS

Russo et al, Amer. Journal of Hospital Pharm., *Lidocaine Anesthesia: Comparison of Iontophoresis, Injection and Swabbing*, vol. 37, 1980, pp. 843-847.

(Continued)

*Primary Examiner* — Tatyana Zalukaeva
*Assistant Examiner* — Imani Hayman
(74) *Attorney, Agent, or Firm* — Nikolai & Mersereau, P.A.; C. G. Mersereau

(57) ABSTRACT

A transdermal system for the delivery of an anesthetic or other active therapeutic agent directly to a selected site of injured skin tissue by iontophoresis is disclosed, which utilizes a transdermal skin-worn patch including a donor electrode chamber containing a donor electrode and an amount of an active agent in a form suitable for transdermal delivery in electrical communication with the donor electrode and a return electrode. The patch also contains a source of electric current connected in a circuit with the donor and return electrode, a current regulating device is optionally provided in the circuit for controlling the electrical output of the patch and at least the donor electrode chamber includes a provision for absorbing a quantity of fluid associated with weepage from adjacent injured skin tissue.

16 Claims, 5 Drawing Sheets

U.S. PATENT DOCUMENTS

| | | |
|---|---|---|
| 2003/0088204 A1* | 5/2003 | Joshi .............................. 604/20 |
| 2004/0267169 A1 | 12/2004 | Sun et al. |
| 2005/0010161 A1 | 1/2005 | Sun et al. |
| 2005/0015042 A1* | 1/2005 | Sun et al. ........................ 604/20 |
| 2005/0148996 A1* | 7/2005 | Sun et al. ...................... 604/501 |
| 2007/0078434 A1* | 4/2007 | Keusch et al. ................ 604/501 |
| 2007/0093743 A1* | 4/2007 | Keusch et al. .................. 604/20 |

OTHER PUBLICATIONS

Phipps et al, Journal of Pharm. Science, *Iontophoretic Delivery of Model Inorganic and Drug Ions*, vol. 78, No. 5, May 1989, pp. 365-369.

* cited by examiner

TRANSDERMAL SYSTEMS FOR THE DELIVERY OF IONIC AGENTS DIRECTLY TO OPEN WOUNDS AND SURGICALLY REPAIRED INCISIONS

CROSS-REFERENCED TO RELATED APPLICATIONS

This application is a non-provisional application claiming the benefit of U.S. Provisional Application Ser. No. 60/865,471, filed Nov. 13, 2006 and which is deemed incorporated by reference herein in its entirety.

STATEMENT REGARDING FEDERALLY SPONSORED RESEARCH OR DEVELOPMENT

Not applicable

BACKGROUND OF THE INVENTION

I. Field of the Invention

The present invention is related generally to transdermal delivery of ionic agents and, more particularly, to the transdermal delivery of local anesthetic agents directly into repaired incisions and skin wounds for the management of pain by the use of an applied electro-motive force (emf), commonly known as iontophoresis.

II. Related Art

The process of iontophoresis was described by LeDuc in 1908 and has since found commercial use in the delivery of ionically charged therapeutic agent molecules such as pilocarpine, lidocaine and dexamethasone. In this delivery method, ions bearing a positive charge are driven across the skin at the site of an electrolytic electrical system anode while ions bearing a negative charge are driven across the skin at the site of an electrolytic system cathode.

Earlier, and some present, iontophoretic devices have been typically constructed of two electrodes attached by adhesive materials to a patient, each connected by a wire to a remote power supply, generally a microprocessor-controlled electrical instrument. More recently, self-contained wearable iontophoretic systems have been developed. These systems are advantageous in that they do not have external wires and are much smaller in size. Examples of such systems can be found in a variety of U.S. patents, including U.S. Pat. Nos. 4,927,408; 5,358,483; 5,458,569; 5,466,217; 5,533,971; 5,605,536; 5,651,768; 5,685,837; 6,421,561; 6,653,014; and 6,745,071. Other examples of wearable systems can be found in patent application publications 2005/0010161; 2005/0015042 and 2004/0267169. These systems are also comprised of two electrodes fixed to patients by means of adhesive materials.

Iontophoretic devices have been used for the delivery of anesthetic agents, in order to create a numbing effect in normal intact skin, to prophylactically minimize pain associated with needlestick insertion or minor surgical procedures. Research has demonstrated that this can be an effective treatment, as exemplified, for example, in a research article by Russo et al. (Lidocaine Anesthesia: Comparison of Iontophoresis, Injection, and Swabbing, Am. J. Hosp Pharm, 1980, 37:843-847). The Russo article concludes that iontophoresis of lidocaine through intact skin as a prophylactic treatment for skin anesthesia, is more effective than topical delivery. A commercially available product for this purpose is Numby Stuff®, sold by Iomed Inc. A similar product, LidoSite® is sold by Vyteris, Inc.

These prior art devices are limited to prophylactic treatment of intact skin, using a short application duration of approximately 10-20 minutes, and current levels averaging at approximately 2-4 mA, to achieve sufficient delivery of anesthetic agent to numb skin in areas of approximately 7-8 $cm^2$ (i.e., using current densities of 250-600 microamps/$cm^2$). Ironically, these higher current levels can themselves serve to cause pain that is intended to be avoided.

The efficiency in which ions are transferred into the body by iontophoresis is much lower than 100%, and is dependent on several factors. For best efficiency, the species to be delivered will carry a charge, so that it will flow in the electric field. Also important for maximum efficiency is to minimize competing ions, which are ions of similar charge to the species desired to be transferred. Competing ions present along with the desired delivery species will lower delivery efficiency, by a proportion related to the relative concentration and size of the competing ions. Also serving to reduce delivery efficiency is ions of opposite charge present in the body, which transfer back to the delivery chamber as a proportion of total charge flow. These efficiency effects are known in the art and published in articles such as Phipps et al, Iontophoretic Delivery of Model Inorganic and Drug Ions, J. Pharm Sci., Vol. 78, No. 5, May 1989, pp 365-369. Even under optimal conditions, delivery efficiency is less than 50%. For positively charged drugs of molecular weight 181-260 daltons, efficiency can be 4.2-23.9%. When there is poor efficiency, current levels must be very high to sustain the desired delivery rate. This is problematic in that high current rates are associated with skin damage.

Traditionally, skin wounds and surgically repaired incisions have been treated with oral medication, and/or localized injections. Limitations associated with oral medications include the stomach discomfort associated with NSAIDS, a non-constant pain management owing to the "ups and downs" of blood levels after oral ingestions, and the dangers of addiction and respiratory depression associated with narcotics. Limitations associated with local injections of anesthetic agents include the pain associated with the injection itself, as well as a short duration of action related with the eventual migration of medication away from the treatment site.

Other approaches to treat incision and wound pain for protracted periods include mechanical delivery of anesthetic fluids through implanted catheters. This technique suffers from the costly and invasive nature of using implantable catheters. Another approach is to utilize topically applied passive patches, as described in U.S. Pat. Nos. 6,383,511 and 6,645,521. This approach suffers from a slow onset of action related to passive delivery.

Little is known about iontophoretic delivery into wounds, particularly fresh wounds where blood or interstitial fluid will weep into the iontophoretic delivery chamber. These fluids will carry both competing ions of like charge into the delivery chamber, and counter ions of opposite charge. Both serve to interfere with and significantly affect delivery efficiency in an adverse manner. Thus, either much higher current levels would be necessary to overcome the affects of competing ions, or effective delivery may not be possible at all.

As indicated, an example of prior art current and current density with regard to intact skin can be derived from the published study by Russo et al (above). In this article, a charge dosage of approximately 4 mA min per square cm provided a skin anesthesia which lasted approximately 25 minutes in a skin area of 7 $cm^2$. Therefore, this art would suggest that 0.16 mA per sq. cm would be sufficient at a constant rate over intact skin. Therefore, it would be expected that a wound care delivery system would require a much greater current density given an unrestricted path for back-flow of counter ions, which would dominate the total current flow. Thus, because of the interference of competing ions and increased sensitivity to current levels associated with injured skin, direct application of ionic agents should not be a viable approach.

To date, no commercial iontophoretic products exist for sustained delivery of anesthetic agents in order to manage pain following an injury such as a skin wound or surgically repaired incision. U.S. Pat. No. 6,560,483 describes an iontophoretic delivery patch for the sustained treatment of an epidermal target site in the form of a border portion patch that surrounds an aperture region which may contain an incision or skin wound. No contact occurs between the delivery patch and skin at the site of the incision or wound. The effectiveness of that device depends on the lateral movement of medication to the open aperture region, where an incision or skin wound may exist, otherwise the site of pain itself is not treated directly. The limitations of this approach include: a high delivery current that would be required to supply enough medication to treat laterally adjacent tissue, and a relatively slow onset of action associated with the time it takes for a lateral transfer of medication to take place. As mentioned previously, the use of high currents is undesirable as skin damage may occur and that can be self-defeating in the administration of pain medications.

Therefore, a need exists for a better means to treat incisions and wounds that is non-invasive, includes sustained release of medication with rapid onset of action and is comfortable to wear.

SUMMARY OF THE INVENTION

In accordance with the present invention, it has been discovered that active agents, particularly local anesthetic agents can be successfully and safely applied directly to repaired incision or other skin wound sites using iontophoresis techniques. Applications can be successful for relatively long periods of time.

Contrary to previous teachings and indications regarding iontophoresis patches covering wounds or incisions, applicants have discovered that the current can actually be reduced to safe levels for injured skin while successfully maintaining a desired agent dosage. Current densities preferably range from about 0.005 to $\leq 0.15$ mA/cm$^2$. Current densities are preferably $\leq 0.10$ mA/cm$^2$ and most preferable are below 0.05 mA/cm$^2$.

The present invention provides a system for the direct application of anesthetic agents by iontophoresis for the treatment of concurrent pain associated with skin incisions and wounds. While many compounds may be useful with the invention, as will be discussed below, it is particularly useful for the delivery of anesthetic agents such as lidocaine, bupivicaine, ropivicaine, and mepivicaine to damaged skin.

The system features a patch device with a donor or delivery chamber that is designed to be applied directly over the incision or wound site and utilizes an electric field to stimulate delivery of the anesthetic agent(s) with a rapid onset of action. The patch is sterilized so that risk of infection is minimal. Additionally, the system delivers medication in a constant manner over an extended period of time. Generally, such time periods are at least 30 minutes and may extend to as many as 96 hours.

Importantly, current (and current densities) with the system of the present invention are maintained at very low levels when compared with known devices, so that sufficient pain reduction is achieved at comfortable levels of current. In this regard, it has been found that the relatively higher total currents and current densities traditionally utilized for skin anesthesia are unacceptable when used over wounds and skin incisions.

According to one aspect, patches of the present invention also incorporate additional features to allow them to absorb excess fluid associated with weepage from an adjacent incision, wound or other lesion. The anesthetic or other active material is contained in an absorbent medium that also has the ability to absorb weepage fluid. Such material may be selected from any natural or synthetic fibrous materials that are inert to or do not react with or interfere with the delivery of the anesthetic material and are not affected by weepage fluid. Such materials may include cellulose and polypropylene fibers, for example. The anesthetic or other active material itself may be contained in a water solution or in a gelled form, for example, as a viscous solution in hydroxypropylmethylcellulose (HPMC).

Illustrative embodiments include two approaches to manage the weepage from a wound: fixed volume and variable volume. The fixed volume approach is a design that incorporates an iontophoretic delivery chamber having a volume that includes unused absorption capacity that does not appreciably change over time. In contrast, the variable volume approach incorporates an iontophoretic delivery chamber that is capable of expanding to absorb fluid material.

One fixed volume approach comprises a delivery pad that is underfilled (or undersaturated), and therefore capable of absorbing excess fluid. This can be accomplished as by providing a delivery pad which is underfilled as illustrated in FIG. 2a. Alternatively, more elaborate means can be utilized with this approach. For example, an expansion volume space of fixed dimensions and unused absorption capacity can be connected to the delivery chamber, as shown by FIG. 2b.

The expansion volume approach for accepting weepage utilizes an iontophoretic delivery chamber capable of expanding or stretching. This can be accomplished using stretchable materials in a delivery chamber as illustrated in FIG. 3. Alternatively, non-stretchable materials configured to shift or accordion or expand in a fan-like (or similar) manner will also serve to expand the chamber to accommodate weepage.

Other embodiments may be used to administer other types of active agents such as ionic anti-microbial compounds or even non-ionic compounds through electro-osmosis. One illustrated embodiment is used for the treatment of acne lesions.

BRIEF DESCRIPTION OF THE DRAWINGS

In the figures wherein like reference characters depict like parts.

DETAILED DESCRIPTION

The detailed description that follows involves a description of certain embodiments which are presented as examples representing the novel concepts of the present invention rather than as limitations on the scope of any of these concepts.

Figure 1:
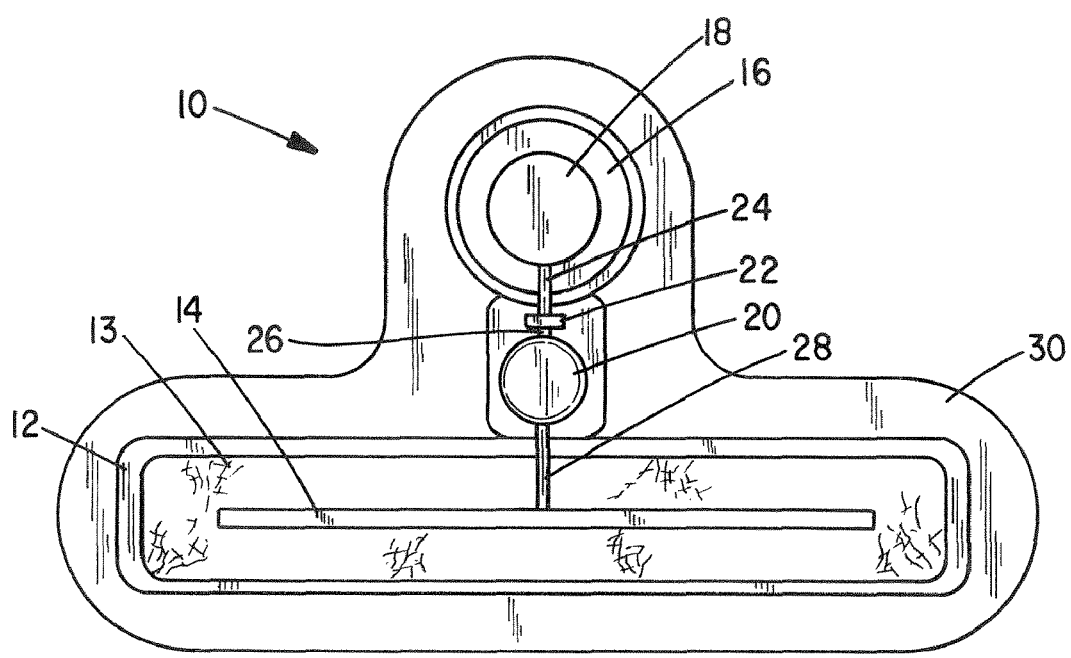
FIG. 1 is a schematic representation showing a top view of a patch (with internal components) usable for the transdermal delivery of anesthetic agents in accordance with the invention.

FIG. 1 depicts a schematic top view of an iontophoretic patch device suitable for the transdermal delivery of anesthetic agents in accordance with the invention. The patch, represented generally by the reference character 10, is shown with internal parts exposed and includes a donor or delivery electrode chamber 12 containing an absorbent pad 13 which includes an amount of an anesthetic agent to be delivered and a donor or delivery electrode shown at 14. The donor electrode chamber contains the active anesthetic agent to be delivered transdermally and is designed to cover an incision or other wound together with an amount of the surrounding skin providing a fixed and known designated contact area. While the donor electrode chamber of FIG. 1 is shown as an elongated, generally rectangular shape, it will be appreciated that any convenient shape of known area may be utilized depending on the desired application of the device, the illustrated shape being a typical shape for treating a linear incision.

The patch 10 then further includes a return or counter electrode chamber 16 containing a return or counter electrode 18. A source of electric current is provided which may be a lithium cell as at 20 or any other suitable device. As an alternative, a galvanic couple may be provided as part of the electrode composition which can supply a relatively constant current for a relatively long time. For example, a galvanic couple having an anode constructed of zinc with a cathode constructed of Ag/AgCl will provide a 1-volt power supply. Current control is optional but preferred, and may be provided as by a resistor, transistor or other electronic current device 22, as is well known in the art, and the elements are connected together in a circuit as by conductive connectors 24, 26, 28. The full circuit is completed when the patch is applied to the skin of a patient in a well known manner. A covering layer or overlay membrane is shown at 30 which is provided with an adhesive coating to adhere the patch 10 to the skin of a user.

Figure 2A:
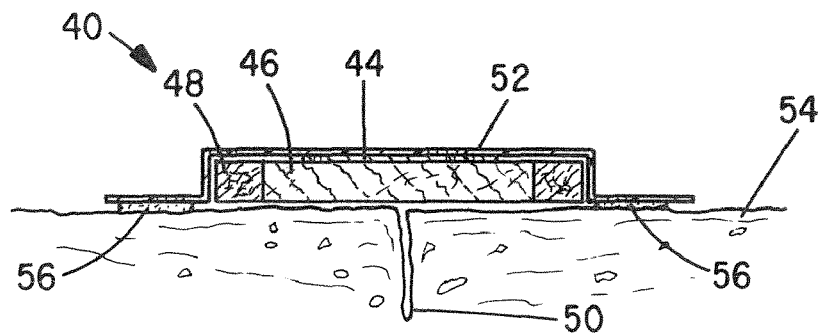
FIG. 2a is a schematic representation showing a section through a delivery pad as it appears attached to the skin of a patient which is underfilled to enable acceptance of weepage volume from an incision or wound.

FIG. 2a depicts a schematic sectional view through a patch 40 as it appears attached to the skin of a patient. The patch 40, similar to patch 10, includes a donor electrode chamber 42 containing a donor electrode 44 and containing an amount of anesthetic agent 46 carried by an absorbent pad 48. The absorbent pad 48 includes an amount of material extending beyond the area occupied by the anesthetic agent at 46 which may be utilized to absorb material weeping from a wound or incision into the patch. Such a wound or incision is illustrated by 50. A covering member layer is shown at 52 which adheres the patch 40 to skin 54 as by a peripheral adhesive layer 56 which also serves to seal the patch and prevent leakage from the wound or incision beyond the patch.

Figure 2B:
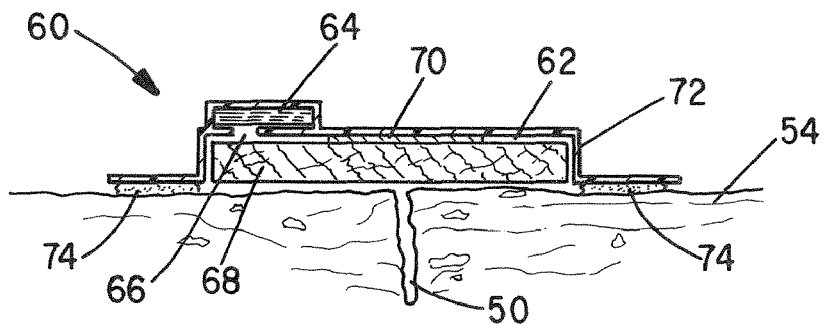
FIG. 2b is a schematic sectional view similar to FIG. 2a through another embodiment of a delivery pad which includes a separate unsaturated portion of the delivery chamber to accept weepage volume.

FIG. 2b depicts an alternate embodiment 60 in which a separate or expansion portion of the donor or delivery chamber 62 is provided at 64 and is in communication with the main donor or delivery chamber 62 through a slotted opening as at 66. The delivery chamber 62 is otherwise filled by the material containing an amount of the anesthetic agent to be delivered at 68, the absorbent material in the expansion chamber 64 being utilized to accommodate weepage material from a corresponding wound or incision 50 to be treated. A donor delivery electrode is shown at 70 and a covering layer 72 is shown peripherally adhering the device 60 to the skin 54 using an adhesive as at 74.

Figure 3:
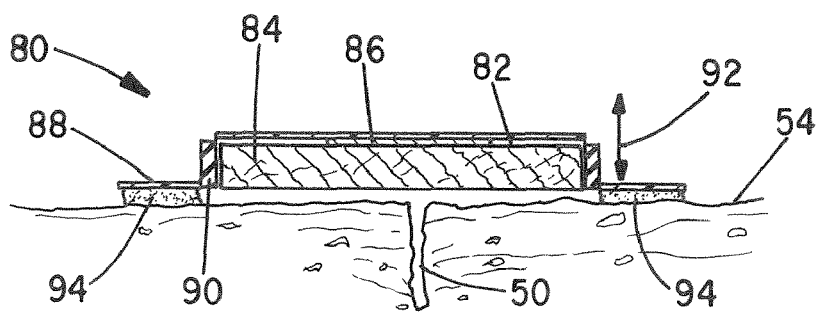
FIG. 3 depicts a sectional schematic view similar to FIG. 2a of yet another embodiment of a delivery pad which includes stretchable chamber walls.

FIG. 3 depicts a different embodiment of a patch device 80 including a delivery or donor chamber 82 filled with an absorbent material containing an amount of an anesthetic agent 84 and a delivery or donor electrode is shown as at 86. The material 84 is one which expands or swells as it takes on or absorbs additional liquid in the form of weepage material from wound or incision 50 and has a relatively large capacity for liquid. The device includes a covering layer 88 which includes an expandable or stretchable area, which may be an elastic band, which enables it to expand as at 90, as shown by the arrow 92. Adhesive holds the device in place on the skin of a patient as at 94.

The preferred anesthetic agents to be delivered include lidocaine, bupivicaine, ropivicaine and mepivicaine. These agents are normally provided in a water solution which is readily absorbed in a delivery pad which is preferably made from or includes an amount of a natural or synthetic fibrous material which is relatively inert to the materials it contacts and the iontophoresis process. The electrodes utilized in the iontophoresis patch itself may be selected from known donor and return or counter electrodes. Typically, the donor electrode may be zinc or silver and the counter electrode may be silver chloride for positively charged anesthetic ions. While many batteries or other sources of AMF to drive the iontophoresis of the patch may be provided, button-type lithium cells have been successfully used.

Figure 4:
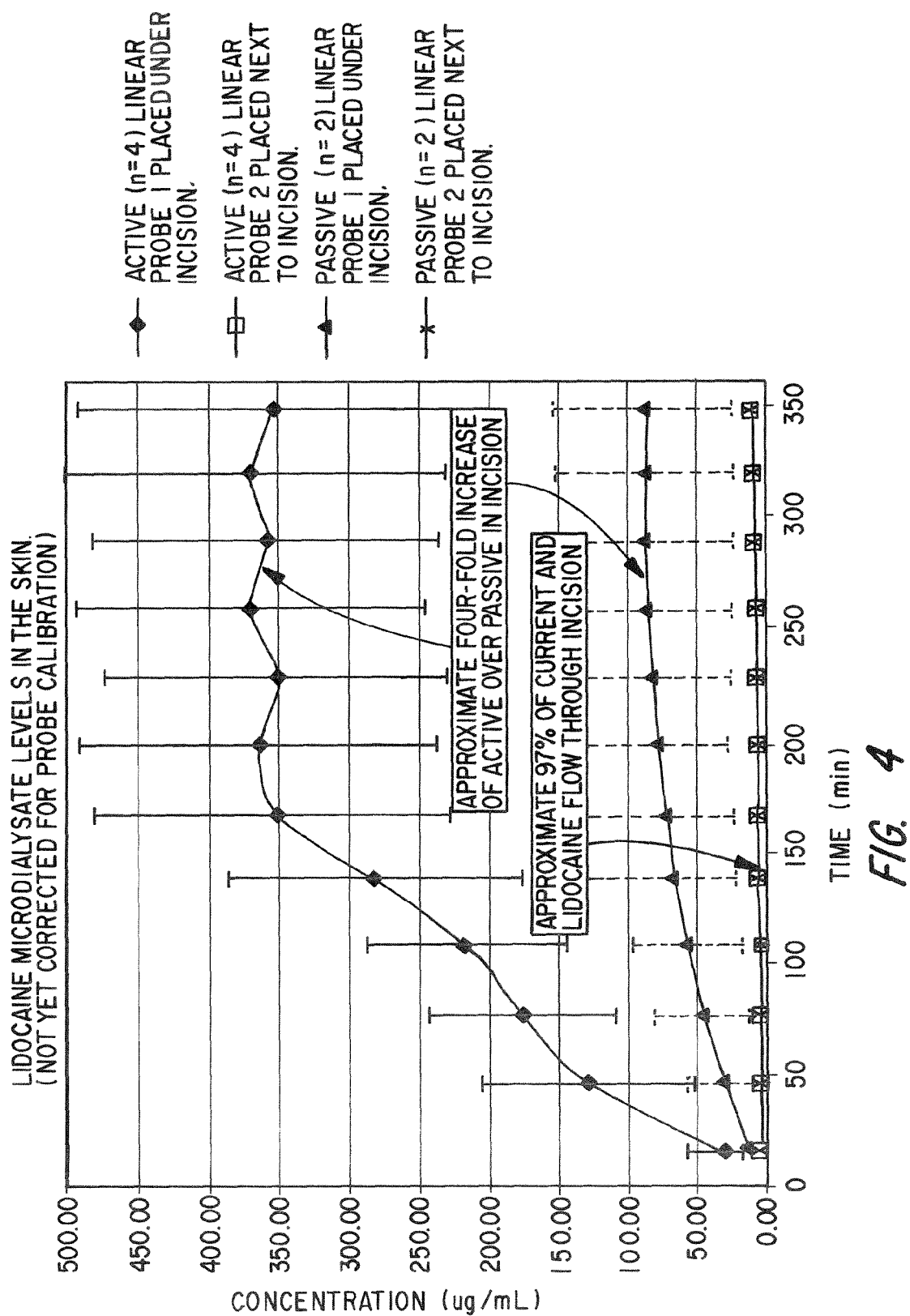
FIG. 4 shows a representation of lidocaine microdialygate levels in the skin represented by plots of lidocaine concentration levels versus time for both active and passive linear probes placed under or next to a surgical incision.
Figure 5:
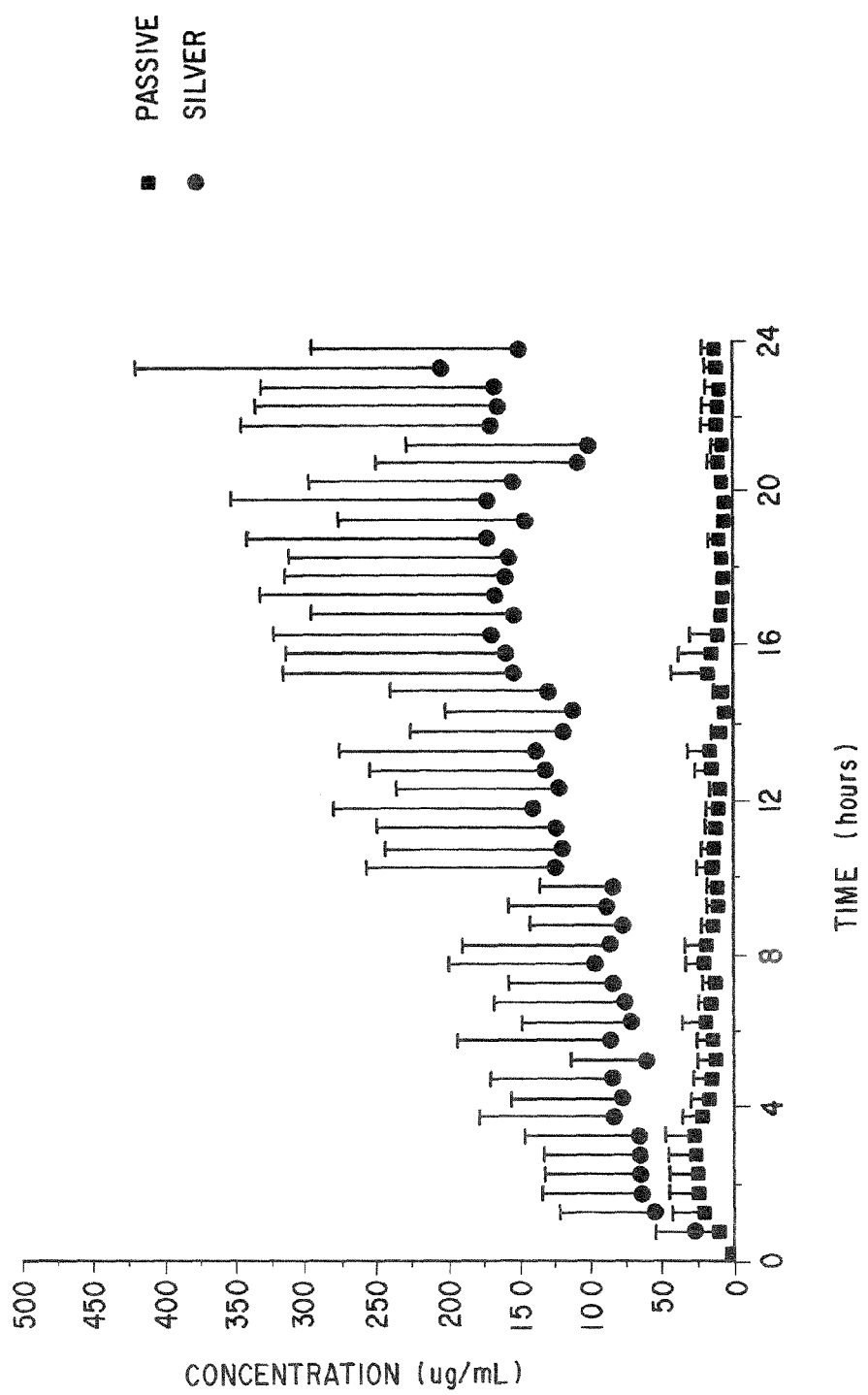
FIG. 5 depicts a comparison of lidocaine penetration in both passive and active (0.15 mA/cm$^2$ current) patches using plots of concentration versus time.

The results of certain examples are displayed in FIGS. 4 and 5 and these will next be presented.

Example 1

In-Vitro Delivery of Lidocaine into an Incision Using Human Cadaver Skin

An incision was made in cadaver skin, which was then sutured closed. A delivery chamber consisting of an absorbent pad saturated with 4% lidocaine was placed over the incision. A zinc donor electrode was connected to the 4 cm$^2$ delivery pad, and a silver chloride counter electrode was placed in a location remote to the delivery chamber, in ionic contact with the cadaver skin by an agarose gel filled with 0.9% saline. To determine whether lidocaine is transferred by iontophoresis, several microdialysis probes were placed in varying locations: under the incision, under the dermis adjacent to the incision, and into an agarose gel at 1 and 4 cm depths underlying the cadaver skin. Current was increased from 0.12 mA for the first two hours to 0.33 mA in hours 2-4 and to 0.54 mA in hours 4-6. As a passive control, the same apparatus was used absent current flow. Concentration of lidocaine sufficient to cause anesthesia was generated in the incision, at all current densities tested. The results of this study are shown in plot form in FIG. 4.

As can be seen from FIG. 4, the use of the iontophoresis patch of the invention accomplishes an approximate four-fold increase in the active material actually reaching the incision where it can administer anesthetic effects. In addition, excellent current flow through the incision is accomplished as also shown by the data in FIG. 4.

Example 2

In-Vivo Delivery of Lidocaine into Surgically Repaired Incisions

An incision was made in hairless rats, which was then sutured closed. A delivery chamber, consisting of an absorbent pad saturated with 4% lidocaine, was placed over the incision. A silver donor electrode was connected to the 2 cm$^2$ delivery pad and a silver chloride counter electrode chamber filled with 0.9% saline was placed on the animal in a location remote to the delivery chamber. To determine whether lidocaine is transferred by iontophoresis, a microdialysis probe was placed in the incision. A total of 0.3 mA of iontophoretic current was applied for 24 hours, with lidocaine concentration monitored within the incision. As a passive control, the same apparatus was used absent current flow. Concentration of lidocaine sufficient to cause anesthesia was generated in the incision for the entire 24-hour period for the active iontophoretic probe. The results of this study are shown in plot form in FIG. 5.

While the present invention is particularly useful for delivery of anesthetic agents, those skilled in the art will recognize that use in other applications is certainly possible. For example, the patches may be used for the delivery of anti-microbial compounds such as silver ion, gentamicin, ampicillin, or kanamycin to prevent infection in open wounds during the healing process.

It will also be recognized that non-ionic compounds may be delivered using a patch in accordance with the present invention through electro-osmosis. Examples of useful non-ionic compounds may be anti-microbial compounds such as benzyl alcohol or anti-acne agents such as benzoyl peroxide.

Patches in accordance with the invention may also be used to delivery anti-acne compounds such as salicylate derivatives into acne lesions, which can become open skin wounds as acne changes from papules to pustules.

Figure 6:
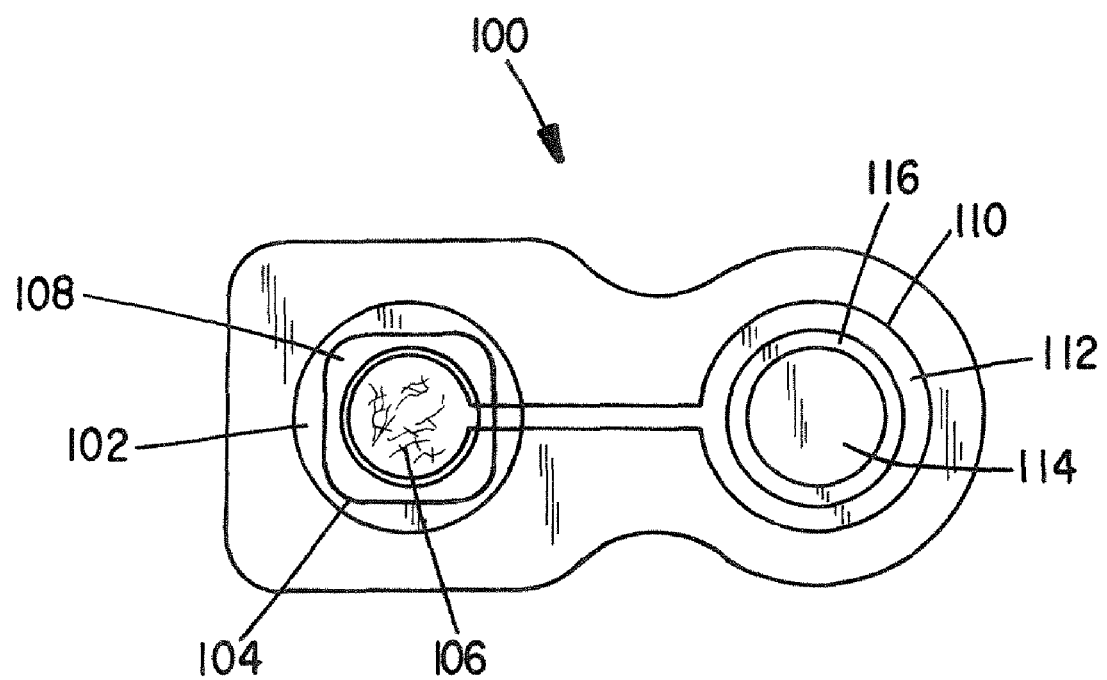
FIG. 6 depicts a top view schematic representation (with internal components) of an acne treatment patch.

One embodiment of a patch suitable for the delivery of agents to treat acne lesions is illustrated in FIG. 6. The patch, generally at 100, includes an anode chamber 102, the contents of which are in electrical communication with an amount of anode electrode material at 104. The anode material may preferably include zinc. The anode chamber 102 further houses an absorbent patch or gel material 106 as has been described above suitable for retaining an amount of an ionic species. An amount of open space 108 is provided in the chamber 102 to accommodate weepage liquid from adjacent lesions. The patch 100 further includes a cathode chamber 110 containing material in electrical communication with an amount of cathode electrode material which may preferably be silver/silver chloride (Ag/AgCl) as at 112. An amount of absorbent material for containing a solution or gel containing a cathode-delivered ionic species is shown at 114 and a peripheral weepage collection space is shown at 116. The electrodes 104 and 112 are connected by a conductor 118 and a current regulating device may optionally also be provided in the circuit (not shown).

When the active agent is negatively charged (such as with salicylate ion), it is preferably placed in the cathode chamber. When the active agent is positively charged (such as with silver ion) or neutral (such as with benzyl alcohol), it is preferably placed in the anode chamber. Whichever chamber contains the active agent is to be placed over the treatment area of skin. The acne patch is typically somewhat smaller in size than an incision patch and one embodiment was about 0.875 inch (2.22 cm) wide by 1.84 inches (4.69 cm) long.

It will be appreciated that the iontophoretic patches of the invention may be provided with the active agent to be delivered contained and stored in the patch or an agent may be separately provided for incorporation at the time of use. The active agent may also be contained in the patch but stored isolated from the electrodes and from the power source during storage prior to use. In this type of patch, the gel or solution containing the active agent is contacted with the delivery system when the patch is activated. Such a system is shown and described in Anderson et al. (U.S. Pat. No. 6,745,071) which is assigned to the same assignee as the present invention and which is deemed incorporated by reference herein in its entirely for any purpose.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A transdermal system for the sustained delivery of an anesthetic agent directly to a selected site of an open skin wound by iontophoresis comprising:
    a transdermal skin-worn patch that is configured to include when applied to an open skin wound:
    (a) a donor chamber containing a donor electrode and a medium for containing an amount of anesthetic agent in a form suitable for transdermal delivery by iontophoresis in electrical communication with said donor electrode and a return electrode;
    (b) a source configured to supply a low-level electric current in said patch that exhibits a low current density as applied to injured skin suitable for safe transdermal delivery of a desired dosage of said anesthetic agent through injured skin for a sustained duration, said source being connected in a circuit with said donor and return electrodes;
    (c) wherein said donor electrode chamber further includes a provision for absorbing a quantity of fluid associated with weepage from adjacent injured skin tissue; and
    (d) wherein said system is configured to deliver medication over a period of at least six hours.

2. A transdermal system as in claim 1 further comprising an amount of anesthetic agent in an epinephrine free formula in said patch.

3. A transdermal system as in claim 1 wherein said anesthetic agent is selected from lidocaine, bupivicaine, ropivicaine and mepivicaine in an epinephrine-free formula.

4. A transdermal system as in claim 2 wherein said anesthetic agent is selected from lidocaine, bupivicaine, ropivicaine and mepivicaine.

5. A transdermal system as in claim 1 wherein said current has a sustained delivery output $\leq 0.15$ mA/cm$^2$ to the skin of a patient.

6. A transdermal system as in claim 1 comprising a current regulating device in said circuit for controlling the electrical output of said patch, and wherein delivery output current is maintained at <0.10 mA/cm$^2$.

7. A transdermal system as in claim 4 wherein said anesthetic agent is lidocaine.

8. A transdermal system as in claim 1 wherein said donor electrode chamber is one of fixed volume that incorporates an absorbent pad for containing said anesthetic agent that has additional capacity to absorb a quantity of weepage fluid upon application to the skin.

9. A transdermal system as in claim 1 wherein said donor electrode chamber includes a pad for containing said anesthetic agent and includes an expansion chamber in communication therewith that includes an absorbent pad that provides additional capacity to absorb a quantity of weepage fluid upon application to the skin.

10. A transdermal system as in claim 1 comprising an expanding donor electrode chamber is provided with an absorbent pad for containing said anesthetic agent, said pad having additional capacity to absorb a quantity of weepage fluid while expanding the volume of said donor electrode chamber upon application to the skin.

11. A transdermal system as in claim 2 wherein said anesthetic agent is contained in a water-based solution.

12. A transdermal system as in claim 2 wherein said anesthetic agent is contained in the form of a gelled material.

13. A transdermal system as in claim 12 wherein said gel comprises hydroxypropylmethylcellulose (HPMC).

14. A transdermal system as in claim 1 wherein said provision for absorbing fluid includes an absorbent pad.

15. A transdermal system as in claim 14 wherein said absorbent pad comprises natural or synthetic fibrous material.

16. A method of administering an ionic therapeutic agent directly to a selected site of an open skin wound comprising:
   (a) causing a skin-worn patch to be positioned over a selected skin site, wherein said patch comprises
      (1) a donor chamber containing a donor electrode and an amount of therapeutic agent in a form suitable for transdermal delivery by iontophoresis in electrical communication with said donor electrode, said patch further comprising a return electrode;
      (2) a source configured to supply a low-level electric current in said patch exhibiting a low current density as applied to injured skin suitable for safe transdermal delivery of a desired dosage of said therapeutic agent through injured skin for a sustained duration of at least 30 minutes, said source being connected in a circuit with said donor and return electrodes;
      (3) wherein said donor electrode chamber further includes a provision for absorbing a quantity of fluid associated with weepage from adjacent injured skin tissue upon application to the skin;
   (b) wherein the donor chamber of said patch is positioned over the desired treatment area; and
   (c) maintaining said patch on said site for at least 30 minutes and up to 96 hours.

\* \* \* \* \*